(12) United States Patent
Bruhn et al.

(10) Patent No.: US 6,958,429 B2
(45) Date of Patent: Oct. 25, 2005

(54) WATER-ABSORBING POLYMERS WITH SUPRAMOLECULAR HOLLOW MOLECULES, METHOD FOR PRODUCING THEM AND USE OF THE SAME

(75) Inventors: Christoph Bruhn, Moers (DE); Edgar Herrmann, Nettetal (DE); Jörg Issberner, Krefeld (DE); Dagmar Kersten, Meerbusch (DE); Richard Mertens, Krefeld (DE); Georg Werner, Toenisvorst (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 157 days.

(21) Appl. No.: 10/775,185

(22) Filed: Feb. 11, 2004

(65) Prior Publication Data

US 2004/0157989 A1 Aug. 12, 2004

Related U.S. Application Data

(63) Continuation of application No. 09/701,564, filed as application No. PCT/EP99/03705 on May 28, 1999.

(30) Foreign Application Priority Data

Jun. 8, 1998 (DE) .......................................... 198 25 486

(51) Int. Cl.[7] .......................... A61F 13/15; C08F 63/91
(52) U.S. Cl. ..................... 604/358; 604/367; 525/54.2; 525/54.24; 525/54.23; 525/54.3; 525/54.4; 424/405; 424/443; 424/486; 424/487; 424/488; 428/304.4; 428/305.5; 428/308.4; 522/6
(58) Field of Search ............................... 604/358, 367; 525/54.2, 54.23, 54.24, 54.3, 54.4; 424/405, 443, 486; 428/304.4, 305.5, 308.4; 522/6

(56) References Cited

U.S. PATENT DOCUMENTS

| | | |
|---|---|---|
| 3,453,257 A | 7/1969 | Parmerter et al. |
| 3,740,391 A | 6/1973 | Williams et al. |
| 4,076,663 A | 2/1978 | Masuda et al. |
| 4,094,833 A | 6/1978 | Johansson et al. |
| 4,153,585 A | 5/1979 | Tessler |
| 4,286,082 A | 8/1981 | Tsubakimoto et al. |
| 4,638,058 A | 1/1987 | Brandt et al. |
| 4,654,039 A | 3/1987 | Brandt et al. |
| 4,666,983 A | 5/1987 | Tsubakimoto et al. |
| 5,134,127 A | 7/1992 | Stella et al. |
| 5,154,713 A | 10/1992 | Lind |
| 5,229,466 A | 7/1993 | Brehm et al. |
| 5,314,420 A | 5/1994 | Smith et al. |
| 5,357,012 A | 10/1994 | Nussstein et al. |
| 5,360,899 A | 11/1994 | Nussstein et al. |
| 5,408,049 A | 4/1995 | Gale et al. |
| 5,409,771 A | 4/1995 | Dahmen et al. |
| 5,433,753 A | 7/1995 | Dahmen et al. |
| 5,455,284 A | 10/1995 | Dahmen et al. |
| 5,538,655 A | 7/1996 | Fauteux et al. |
| 5,575,939 A | 11/1996 | Dahmen et al. |
| 5,672,633 A | 9/1997 | Brehm et al. |
| 5,954,921 A | 9/1999 | Dahmen et al. |
| 6,133,369 A | 10/2000 | Houben et al. |
| 6,229,062 B1 | 5/2001 | Mandell et al. |

FOREIGN PATENT DOCUMENTS

| | | |
|---|---|---|
| DE | 27 06 135 | 8/1978 |
| DE | 40 20 780 | 8/1991 |
| DE | 44 40 236 | 5/1996 |
| DE | 195 20 989 | 12/1996 |
| DE | WO 97/09354 | 3/1997 |
| DE | 195 33 269 | 3/1997 |
| EP | 0 317 106 | 5/1989 |
| EP | 334 515 A1 | 9/1989 |
| EP | 369 023 A1 | 9/1990 |
| EP | 392 608 B1 | 10/1990 |
| EP | 0 483 380 | 5/1992 |
| EP | 710 675 A2 | 5/1996 |
| EP | 780 401 A1 | 6/1997 |
| EP | 806 195 A1 | 11/1997 |
| GB | 932389 | 8/1960 |
| JP | 61 283601 | 12/1986 |
| JP | 04 163372 | 6/1992 |
| WO | 89/02698 | 4/1989 |
| WO | WO 94/09043 | 4/1994 |
| WO | 94/22500 | 10/1994 |
| WO | WO 94/22501 | 10/1994 |
| WO | 96/17681 | 6/1996 |

OTHER PUBLICATIONS

A. P. Croft, et al., Tetrahedron, vol. 39, No. 9, pp. 1417–1474, "Synthesis of Chemically Modified Cyclodextrins", 1983.

A. Harada, et al., J. Org. Chem. vol. 58, No. 26, pp. 7524–7528, "Preparation and Characterization of Polyrotaxanes Containing Many Threaded α–Cyclodextrins", 1993.

A. Norberg, et al., Gerontology, vol. 30, pp. 261–266, "The Urine Smell Around Patients with Urinary Incontinence", 1984.

A. Zlatkis, et al., Analytical Chemistry, vol. 45, No. 4, pp. 763–767, "Profile of Volatile Metabolites in Urine by Gas Chromatography–Mass Spectrometry", Apr. 1973.

G. Wenz, Angew. Chem., vol. 106, pp. 851–870, "Cyclodextrine ALS Bausteine Supramolekularer Strukturen Und Funkionseinheiten", 1994.

(Continued)

Primary Examiner—Samuel A. Acquah
(74) Attorney, Agent, or Firm—Oblon, Spivak, McClelland, Maier & Neustadt, P.C.

(57) ABSTRACT

The invention relates to absorbent polymers based on optionally partially neutralised, monoethylenically unsaturated, acid group-carrying monomers. The surfaces of said polymers are re-cross-linked. The inventive polymers also have cyclodextrines and/or cyclodextrine derivatives which are covalently and/or ionically bonded and/or included therein.

31 Claims, No Drawings

OTHER PUBLICATIONS

C. Roussel, et al., Journal of Chromatography A, No. 704, pp. 67–74, "Cationic β–Cyclodextrin: A New Versatile Chiral Additive for Separation of Drug Enantiomers by High–Performance Liquid Chromatography", 1995.

R. H. Waring, et al., Xenobiotica, vol. 1.7, No. 11, pp. 1363–1371, "The Chemical Nature of the Urinary Odour Produced by Man After Asparagus Ingestion", 1987.

T. Takeuchi, et al., Chromatographia, vol. 38, No., 7/8, pp. 453–455, "Liquid Chromatography of Cyclodextrins with Indirect Photometric Detection of Phenolphthalein Inclusion Complexes", Apr. 1994.

Denter, U., et al., "Textiles with Multifunctional Propeties by Chemical Bonding of Cyclodextrines", 38th International Detergency Conference, 1998, pp. 122–126.

WATER-ABSORBING POLYMERS WITH SUPRAMOLECULAR HOLLOW MOLECULES, METHOD FOR PRODUCING THEM AND USE OF THE SAME

This application is a Continuation Application of U.S. Ser. No. 09/701,564, filed on Dec. 7, 2000 now allowed, which is the national stage of International Application PCT/EP99/03705, filed May 25, 1999.

The invention relates to absorbents, preferably for water and aqueous liquids, which absorbents are based on polymers absorbing aqueous liquids, wherein cyclodextrin or cyclodextrin derivatives have been incorporated ionically, covalently and/or as a result of mechanical inclusion.

Commercially available superabsorbing polymers essentially are crosslinked polyacrylic acids, crosslinked starch/acrylic acid graft copolymers, crosslinked hydrolyzed starch/acrylonitrile graft copolymers, crosslinked poly(maleic anhydride-co-isobutylene), or mixtures of various of the above-mentioned crosslinked polymers, wherein the carboxylic groups have been subjected to partial neutralization with sodium and/or potassium ions.

Such polymers find use e.g. in hygiene articles capable of absorbing body fluids such as urine or in materials for cable sheathings where they absorb large amounts of aqueous liquids and body fluids such as urine or blood with swelling and formation of hydrogels. Furthermore, the absorbed amount of liquid must be retained under a pressure typical of use. During the further technical development of superabsorbing polymers, the pattern of requirements to be met by these products has changed significantly over the years. To date, the development of superabsorbers has been forced particularly with respect to the amount of absorbed liquid and pressure stability.

Such crosslinked polymer products based on monomers containing acid groups are obtained by using one or more primary crosslinkers and one or more secondary crosslinkers and exhibit a combination of properties, namely, high retention, high absorption under pressure, low solubles, and rapid absorption of liquid, which has not been achieved so far. When used in hygiene articles, these crosslinked polymer products have the advantage that secreted fluids, once absorbed by the polymer product, can no longer contact the skin. Thus, skin lesions such as diaper dermatitis can largely be avoided. Such comfort can even be increased by absorbing malodorous compounds.

According to Römpp Chemie Lexikon, the content of urine components is subject to physiological fluctuations; also, particular substances are secreted at concentrations varying within a daily period, so that more precise data on the-urine composition invariably are related to the so-called 24 hour urine which, in a healthy adult, contains e.g. urea (average 20 g), uric acid (0.5 g), creatinine (1.2 g), ammonia (0.5 g), amino acids (2 g), proteins (60 mg), reducing substances (0.5 g, about 70 mg of which are D-glucose or urine sugar), citric acid (0.5 g) and other organic acids, as well as certain vitamins (C, $B_{12}$ etc.). The following inorganic ions are present: $Na^+$ (5.9 g), $K^+$ (2.7 g), $NH_4^+$ (0.8 g), $Ca^{2+}$ (0.5 g), $Mg^{2+}$ (0.4 g); $Cl^-$ (8.9 g), $PO_4^{3-}$ (4.1 g), $SO_4^{-2}$ (2.4 g). The dry content is between 50 and 72 g. Inter alia, alkylfurans, ketones, lactones, pyrrole, allyl isothiocyanate, and dimethyl sulfone have been recognized as volatile components of urine. Most of the volatile components are molecules having a molar mass below about 1000 g/mol and a high vapor pressure.

Volatile components of urine have also been investigated by, inter alia, A. Zlatkis et al. (Anal. Chem. Vol. 45, 763ff.).

It is also well-known that consumption of asparagus results in an increase of the concentration of organic sulfur-containing compounds in human urine (R. H. Waring, Xenobiotika, Vol. 17, 1363ff.). In patients who are subject to specific diets and generally, in patients who ingest specific medications, or in elderly individuals with decreasing kidney function, the urine may include malodorous substances. Patients suffering from urine incontinence have an increased secretion of ureases which convert the urea contained in urine, thereby liberating toxic ammonia. Also, a pathological change is well-known which is referred to as fish smell syndrome. It results from an increased secretion of quaternary ammonium compounds.

Previous approaches of achieving an odor reduction in incontinence products are based on reducing the concentration of free ammonia. Basically, there are two approaches to this end: preventing additional production of ammonia from urea degradation by suitable urease inhibitors (A. Norberg et al., Gerontology, 1984, 30, 261ff.), or by protonating free ammonia and binding thereof in the form of a carboxylate ammonium salt. This method is disadvantageous in that essentially, merely ammonia and other nitrogen-containing components can be controlled. Malodorous compounds lacking basic groups, e.g. thiols, are still capable of entering the vapor space.

It is well-known to those skilled in the art that certain hollow molecules, also referred to as endohedral or concave molecules, are capable of incorporating other, mostly smaller, so-called guest molecules, thereby forming a host-guest complex. Such complex formation has an effect on the chemical and physical properties of both guest and host molecule. These hollow-forming molecules include the cyclodextrins.

Cyclodextrins are formed during starch degradation by *Bacillus macerans* or *Bacillus circulans* under the action of cyclodextrin glycosyl transferase. They are comprised of 6, 7, 8 or 9 glucose units α-1,4-linked to form a ring (α-, β- or γ-cyclodextrins). They are capable of entrapping hydrophobic guest molecules in varying amounts up to saturation ("molecular encapsulation"), e.g. gases, alcohols or hydrocarbons. The use of cyclodextrins as host molecule is reported comprehensively in the work of J. Szejtli (Cyclodextrin Technology, Kluwer Academic Publishers, 1988).

Also, the production of polymers containing cyclodextrins is already known. Thus, EP-A-0,483,380 obtains cyclodextrin-containing polymers by copolymerizing cyclodextrins bearing aldehyde groups with polyvinyl alcohol.

Crosslinked, water-swellable, hydrophilic bead polymers made of hydroxyalkylcyclodextrins and epichlorohydrin or polyepoxide type crosslinkers are known from U.S. Pat. No. 5,360,899. These crosslinkers involve a carcinogenic potential and therefore, such products cannot be used in hygiene articles. These cyclodextrins immobilized by polymerization are used as packing and separating material in chromatographic separation columns.

Furthermore, water-swellable, hydrophilic bead polymers made of cyclodextrins bearing glycidyl or methacrylate groups and optionally other comonomers such as hydroxyethyl acrylate are known from U.S. Pat. No. 5,357,012. Likewise, these cyclodextrins immobilized by polymerization are used as packing and separating material in chromatographic separation columns.

DE-A-195 20 989 describes covalent binding of reactive cyclodextrin derivatives having at least one nitrogen-containing heterocycle to polymers bearing at least one nucleophilic group. Polymers linked to cyclodextrins according to this method must have nucleophilic groups such as OH, NH, or SH groups. Also, polymerizable cyclodextrin derivatives are mentioned which, after suitable modification, are copolymerized with other monomers, e.g. ethylenically unsaturated compounds. As noted in this publication, the products according to the above-mentioned US patent specifications U.S. Pat. No. 5,357,012 and U.S. Pat. No. 5,360,899 involve the drawback that cyclodextrin incorporation is difficult to control in spatial terms and that cyclodextrins fixed inside the polymers are no longer available for utilization. The use of polymers, which include cyclodextrin derivatives, as superabsorbing materials is not mentioned.

Inter alia, the use of cyclodextrins in hygiene products is known from EP-A-806,195, WO 94/22501, and WO 94/22500. Therein, the cyclodextrins are employed to absorb odors. In those cases where the cyclodextrins or cyclodextrin complexes are not bound to the powdered absorbent, demixing during storage or transportation of the hygiene articles may occur. As a result, the effectiveness of the cyclodextrins as odor absorbent may be lost due to demixing between absorbent and cyclodextrins.

To achieve improved adhesion on powdered absorbents, WO 94/22501 teaches addition of polyethylene glycols or other linear polymers to cyclodextrin in a "melt" or in solution and subsequent spraying on the powdered absorbent. However, as is well-known to those skilled in the art, linear polymers have a marked tendency to "thread" into the cyclodextrin cavity, which fact is advantageously utilized in supramolecular chemistry in order to produce e.g. rotaxans or catenanes (cf. the documents U.S. Pat. No. 5,538,655; G. Wenz, Angew. Chem. 1994, 106, 851). Typically, the linear polymers have a molecular weight (m.w.) of more than 200. Also, suitable polymers are e.g. polyethylene glycol (PEG), polypropylene oxide (PEO) and polyethyleneimine. Multiple cyclodextrins can be threaded on a linear polymer chain; Harada et al. (J. Org. Chem. 58, 1993, 7524–28) report that 20 cyclodextrins can be threaded on a polyethylene glycol having an average molecular weight of 2000 g/mol. Therefore, the process described in WO 94/22501 is particularly disadvantageous, because the cyclodextrin cavities after such a polyethylene glycol pretreatment are no longer quantitatively available for absorbing malodorous compounds.

The invention therefore is based on the object of providing polymer products capable of absorbing water or aqueous liquids, and capable of binding malodorous organic compounds such as occurring e.g. in urine or other fluids secreted from the body, and methods of producing same.

The polymer products should not involve the drawbacks of prior art and enable a preferably uniform, marked reduction of gaseous, malodorous compounds released during use. Moreover, a largely stable dispersion of the deodorant component in the absorbent should be achieved, i.e., demixing prior to and during use should be avoided as much as possible. In addition, binding of the deodorant component should not be effected by using carcinogenic or otherwise hazardous substances. Furthermore, the effectiveness of the deodorant component in the absorbent should be independent of its location, i.e., whether inside the polymer or at the surface thereof.

According to the invention, said object is accomplished by providing polymers based on crosslinked monomers bearing optionally partially neutralized acid groups, which polymers have cyclodextrins and/or derivatives thereof bound ionically and/or covalently and/or incorporated therein.

As a result of the inventive binding to the preferably powdered polymer, the cyclodextrin component can be extracted by the liquid to be absorbed to only a lesser extent, or, in the dry state, undergoes demixing to only a lesser extent. Despite the intimate linkage with the crosslinked absorber bearing acid groups, the polymer according to the invention surprisingly shows excellent absorption of odors which is even enhanced compared to unbound cyclodextrin. In particular, the absorbent polymers exhibit high absorption of odors even in those cases where the cyclodextrin is fixed inside the absorber. This can be established by an effective reduction in the gas concentration of malodorous substances.

Moreover, the polymer products of the invention are excellently suited for incorporating active substances, and when used, these active substances can optionally be released in a controlled fashion. By incorporation in the absorbents of the invention, the stability of sensitive active substances is markedly improved.

According to the invention, $\alpha,\beta,\gamma$ type cyclodextrins and derivatives thereof are suitable.

The cyclodextrins have the following recurring structure:

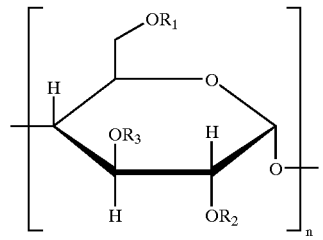

The anhydroglucose units are linked in a cyclic, glycosidic fashion to form rings, wherein the residues $R_1$ through $R_3$ are the same or different, represent H or $C_1$–$C_4$ alkyl, and $\alpha$-cyclodextrin: n=6, $\beta$-cyclodextrin: n=7, $\gamma$-cyclodextrin: n=8, $\delta$-cyclodextrin: n=9. In cyclodextrin derivatives, n different substituents per residue ($R_1$–$R_3$) are possible which may be the same or different.

Above all, those derivatives are possible which permit chemical linkage by ionic or covalent binding to the monomer bearing acid groups or to the corresponding polymer. Covalent linkages preferably are via C—C bonds as, for example, with cyclodextrin derivatives having ethylenically unsaturated groups incorporated covalently in the polymer chain already during polymerization of the monomers. For example, such groups are (meth)acrylic, (meth)allyl and vinyl groups. According to the invention, however, covalent linkage of the cyclodextrin component to the polymer of ethylenically unsaturated monomers is also possible subsequent to polymerization via ether, amide or ester groups.

Ionic binding of the cyclodextrin derivatives can be effected using anionic or cationic groups, with cationic groups being preferred. Frequently, it is advantageous when the cyclodextrin molecules have multiple substitutions with ionic groups. Examples of anionic groups are carboxylate, sulfate and sulfonate groups. Examples of cationic groups are quaternary grous containing nitrogen.

Ionic cyclodextrins can be produced by reacting cyclodextrin derivatives with reactive compounds such as chloroacetic acid, sodium chloroacetate, maleic acid, maleic anhydride, and succinic anhydride. In an aqueous solution, these reaction products, e.g. carboxymethylcyclodextrin, carry a negative charge in a basic medium due to the carboxylate group.

Cyclodextrin derivatives to be used according to the invention and having at least one nitrogen-containing heterocycle can be produced according to the teaching of DE-A-195 20 98, A1, the disclosure of which is hereby incorporated by reference. In this way, cyclodextrin derivatives can be obtained, which include another group active towards nucleophilic groups. These derivatives can undergo direct reaction with polymers bearing nucleophilic groups. Examples of nucleophilic groups are —OH, —NH or —SH groups.

Other chemically modified cyclodextrins to be used according to the invention can be obtained as described in A. P. Croft and R. A. Bartsch, Tetrahedron Vol. 39, No. 9, pp. 1417–1473. They are obtained by reacting nitrogen-containing compounds having at least one functional group capable of reacting with the hydroxyl groups of the cyclodextrins to form ether, ester or acetal groups.

Cationic cyclodextrins such as described in Ch. Roussel, A. Favrou, Journal of Chromatography A, 704 (1995), 67–74, are particularly preferred. They are obtained by reacting cyclodextrin with e.g. N-(3-chloro-2-hydroxypropyl)-N,N,N-trimethylammonium chloride. The cyclodextrins described in the above publication have a degree of substitution of 0.2.

The ionic cyclodextrins including at least one nitrogen-containing aliphatic residue, which can be used according to the invention, may also be produced e.g. according to the methods described in U.S. Pat. Nos. 3,740,391; 4,153,585 and 4,638,058. The disclosure of the above-mentioned publications is hereby incorporated by reference.

For example, N,N-dimethylaminoethyl (meth)acrylate, N,N-dimethylaminopropyl (meth)acrylate, N,N-dimethylaminoethyl(meth)acrylamide, and N,N-dimethylaminopropyl(meth)acrylamide, or the quaternary derivatives thereof obtained by reaction with alkyl halides may be mentioned as suitable monomers. Preferably, N,N-dimethylaminoethyl acrylate (ADAME or ADAME-quat.) and N,N-dimethylaminopropylacrylamide (DIMAPA or DIMAPA-quat.) are employed.

Here, the compound of formula I undergoes reaction:

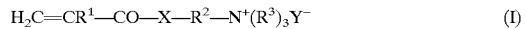
$$H_2C=CR^1-CO-X-R^2-N^+(R^3)_3Y^- \quad (I)$$

wherein $R^1$=H, $CH_3$, $R^2$=$C_2$–$C_4$ alkylene group, $R^3$=H, $C_1$–$C_4$ alkyl group,

X=O, NH,

Y=Cl, $SO_4$.

The average degree of substitution (DS value) per anhydroglucose unit for substituents containing nitrogen can be determined according to methods known from literature using elemental analysis as described e.g. in U.S. Pat. No. 5,134,127 and U.S. Pat. No. 3,453,257 for substituents containing sulfur or nitrogen. When using the synthetic methods described in U.S. Pat. Nos. 3,740,391 and 4,153, 585, the DS value can be varied within wide limits.

3 hydroxyl groups per anhydroglucose unit of a cyclodextrin are capable of undergoing further reaction. Therefore, the degree of substitution e.g. in case of β-cyclodextrin can be between 0.05 and 3 at maximum. A degree of substitution below 0.05 indicates that a mixture of non-modified cyclodextrin and chemically modified cyclodextrin is present.

According to the invention, the degree of substitution (DS) of the cyclodextrin derivatives is 0.005–2, preferably 0.05–1.5.

In addition to the above-mentioned groups required for binding to the polymer, the cyclodextrins may also contain other substituents having no reactivity towards the polymer.

For example, these include reaction products of cyclodextrins with alkylating agents, e.g. $C_1$–$C_{22}$ alkyl halides, e.g. methyl chloride, ethyl chloride, butyl chloride, butyl bromide, benzyl chloride, lauryl chloride, stearyl chloride, or dimethyl sulfate, or reaction products of cyclodextrins with alkylene oxides such as ethylene oxide, propylene oxide, butylene oxide, or styrene oxide.

The amount of cyclodextrin or derivatives thereof to be employed according to the invention is 0.01–50 wt.-%, preferably 0.1–30 wt.-%, more preferably 0.5–10 wt.-%, relative to the total amount of polymer.

Well-known processes are possible for polymerizing the polymers of the invention optionally having superabsorbent properties, e.g. bulk polymerization, solution polymerization spray polymerization, inverse emulsion polymerization, and inverse suspension polymerization.

Preferably, a solution polymerization is performed using water as solvent. The solution polymerization may be conducted in a continuous or batchwise fashion. The prior art includes a broad spectrum of possible variations with respect to concentration conditions, temperatures, type and amount of initiators and of secondary catalysts. Typical processes have been described in the following patent specifications: U.S. Pat. No. 4,286,082; DE 27 06 135, U.S. Pat. No. 4,076,663, DE 35 03 458, DE 40 20 780, DE 42 44 548, DE 43 23 001, DE 43 33 056, DE 44 18 818 which hereby are incorporated as disclosure of the process according to the invention.

Preferably, aliphatic, optionally substituted $C_2$–$C_{10}$, preferably $C_2$–$C_5$ carboxylic acids or sulfonic acids, such as acrylic acid, methacrylic acid, crotonic acid, isocrotonic acid, maleic acid, fumaric acid, itaconic acid, vinylacetic acid, vinylsulfonic acid, methallylsulfonic acid, 2-acrylamido-2-methyl-1-propanesulfonic acid, as well as the alkali and/or ammonium salts or mixtures thereof are possible as ethylenically unsaturated monomers containing acid groups. It is preferred to use acrylic acid and its alkali and/or ammonium salts and mixtures thereof. Furthermore, it is also possible to use monomers being hydrolyzed to form acid groups as late as subsequent to the polymerization, e.g. the corresponding nitrile compounds.

In order to modify the polymer properties, up to 40 wt.-% of monomers other than the monomers containing acid groups, which are soluble in the aqueous polymerization batch, such as acrylamide, methacrylamide, acrylonitrile, (meth)allyl alcohol ethoxylates, and mono(meth)acrylic acid esters of polyhydric alcohols or ethoxylates can optionally be used.

Minor amounts of crosslinking monomers having more than one reactive group in their molecules are copolymerized together with the above-mentioned monomers, thereby forming partially crosslinked polymer products which are no longer soluble in water but merely swellable. Bi- or multi-functional monomers, e.g. methylenebisacryl- or -methacrylamide, or ethylenebisacrylamide may be mentioned as crosslinking monomers, and also, allyl compounds such as allyl (meth)acrylate, alkoxylated allyl (meth)acrylate reacted preferably with from 1 to 30 mol of ethylene oxide units, triallyl cyanurate, maleic acid diallyl ester, polyallyl esters, tetraallyloxyethane, triallylamine, tetraallylethylenediamine, allyl esters of phosphoric acid or phosphorous acid, and also, the N-methylol compounds of unsaturated amides such as methacrylamide or acrylamide and the ethers derived therefrom, as well as esters of polyols and alkoxylated polyols with unsaturated acids, such as diacrylates or triacrylates, e.g. butanediol or ethylene glycol diacrylate, polyglycol di(meth)acrylates, trimethylolpropane triacrylate, di- and triacrylate esters of trimethylolpropane preferably oxyalkylated (ethoxylated) with 1 to 30 mol alkylene oxide, acrylate and methacrylate esters of glycerol and pentaerythritol, and of glycerol and pentaerythritol preferably oxyethylated with 1 to 30 mol ethylene oxide. It is preferred to use triallylamine, acrylates of polyhydric alcohols or alkoxylates thereof, and methallyl alcohol acrylates or alkoxylates thereof. The ratio of crosslinking monomers is from 0.01 to 3.0 wt.-%, preferably from 0.05 to 2.0 wt.-%, and more preferably from 0.05 to 1.5 wt.-%, relative to the total weight of the monomers.

The optional neutralization of the acidic monomers according to the polymerization process of the invention can be performed in various ways. On the one hand, according to the teaching of U.S. Pat. No. 4,654,039, the polymerization may be conducted directly with the acidic monomers, with neutralization being effected subsequently in the polymer gel. Preferably, the acid groups of the monomers are already neutralized to 20–95%, preferably 50–80% prior to polymerization, in which case they are present as sodium and/or potassium and/or ammonium salts at the time polymerization is begun. It is preferred to use those bases for neutralization which do not adversely affect the subsequent polymerization. It is preferred to use sodium or potassium hydroxide solution and/or ammonia, with sodium hydroxide solution being particularly preferred; addition of sodium carbonate, potassium carbonate or sodium bicarbonate may have an additional positive effect as taught in U.S. Pat. Nos. 5,314,420 and 5,154,713. Before initiating the polymerization in this adiabatic solution polymerization, the partially neutralized monomer solution is cooled to a temperature of below 30° C., preferably below 20° C. The other polymerization processes comply with the temperatures known from prior art as apparent from the literature below.

The polymer products of the invention may optionally contain water-soluble natural or synthetic polymers as a basis for grafting in amounts up to 30 wt.-%. Inter alia, these include partially or completely saponified polyvinyl alcohols, starch or starch derivatives, cellulose or cellulose derivatives, polyacrylic acids, polyglycols, or mixtures thereof. The molecular weights of the polymers added as basis for grafting must be adapted to the circumstances of the polymerization conditions. In the event of an aqueous solution polymerization, for example, it may be necessary for viscosity reasons to employ low to medium molecular weight polymers, whereas this factor plays a minor role in a suspension polymerization.

In addition to polymers obtained by crosslinking polymerization of partially neutralized acrylic acid, those are preferably used which are obtained by employing starch or polyvinyl alcohol as graft basis.

The polymerization process of the invention can be initiated by various conditions, e.g. by irradiating with radioactive, electromagnetic or ultraviolet radiation, or by a redox reaction of two compounds, e.g. sodium hydrogen sulfite with potassium persulfate, or ascorbic acid with hydrogen peroxide. The thermally induced decomposition of a so-called free-radical initiator such as azobisisobutyronitrile, sodium peroxodisulfate, t-butyl hydroperoxide, or dibenzoyl peroxide is suitable as well. Furthermore, a combination of some of the above-mentioned polymerization initiators is possible.

Preferably, the polymer products of the invention are produced according to two methods: According to the first method, the partially neutralized acrylic acid is converted to a gel by means of free-radical polymerization in aqueous solution and in the presence of crosslinkers and optional polymer additives, which gel is subsequently crushed and dried until a powdered, flowable state is reached, milled, and screened to the desired particle size. The solution polymerization may be conducted in a continuous or batchwise fashion. The patent literature includes a broad spectrum of possible variations with respect to concentration conditions, temperatures, type and amount of initiators, as well as a variety of secondary crosslinking options. Typical processes have been described in the following patent specifications: U.S. Pat. Nos. 4,076,663; 4,286,082; DE 27 06 135, DE 35 03 458, DE 35 44 770, DE 40 20 780, DE 42 44 548, DE 43 23 001, DE 43 33 056, DE 44 18 818, the disclosure of which is hereby incorporated by reference.

The inverse suspension and emulsion polymerization process may also be used to produce the polymer products of the invention. According to this process variant, an aqueous, partially neutralized solution of acrylic acid is dispersed in a hydrophobic organic solvent using protective colloids and/or emulsifiers, and the polymerization is initiated using free-radical initiators. The crosslinkers are either dissolved solved in the monomer solution and pre-charged together with same or added separately and optionally during polymerization. The optionally present polymeric grafting bases are added via the monomer solution or by directly placing in the oil phase. Subsequently, the water is removed azeotropically from the mixture, and the polymer product is filtrated and optionally dried.

Using the process of subsequent surface crosslinking, the polymer products according to the invention are improved in their pattern of properties, particularly in their absorption of liquid under pressure, so that the well-known phenomenon of "gel blocking" is suppressed, where slightly swollen polymer particles adhere to each other, thereby impeding further absorption of liquid and distribution of liquid in the absorbent articles. In this secondary crosslinking, the carboxyl groups of the polymer molecules are crosslinked at the surface of the polymer particles at elevated temperature using crosslinking agents. Inter alia, methods of secondary crosslinking have been described in the following publications: DE 40 20 780, EP 317,106 and WO 94/9043. According to the invention, all those surface crosslinking agents known to a person skilled in the art from U.S. Pat. No. 5,314,420, page 8, lines 3–45, may be employed advantageously in combination with a crosslinker used during polymerization or a combination of crosslinkers. As a rule, these compounds contain at least two functional groups capable of reacting with carboxylic acid or carboxyl groups. Alcohol, amine, aldehyde, and carbonate groups are preferred and also, crosslinker molecules having multiple different functions are employed. Preferably, polyols, polyamines, polyaminoalcohols, and alkylene carbonates are used. Preferably, one of the following crosslinking agents is used: ethylene glycol, diethylene glycol, triethylene glycol, polyethylene glycol, glycerol, polyglycerol, propylene glycol, diethanolamine, triethanolamine, polypropylene glycol, block copolymers of ethylene oxide and propylene oxide, sorbitan fatty acid esters, ethoxylated sorbitan fatty acid esters, trimethylolpropane, ethoxylated trimethylolpropane, pentaerythritol, ethoxylated pentaerythritol, polyvinyl alcohol, sorbitol, ethylene carbonate, propylene carbonate. It is particularly preferred to use polyols and ethylene carbonate as surface crosslinking agents. The crosslinking agent is employed in an amount of from 0.01 to 30 wt.-%, preferably 0.1–10 wt.-%, relative to the polymer to be crosslinked.

Following polymerization, the polymer product is dried, milled, screened for the respective grain fraction favorable in application-technical terms, and subsequently subjected to surface crosslinking. In some cases, however, it has proven beneficial to add the surface secondary crosslinkers at an early stage prior to drying the polymer gel or prior to crushing the partially or predominantly dried polymer. Secondary crosslinking to be performed according to the invention has been described in U.S. Pat. No. 4,666,983 and DE 40 20 780 which hereby are incorporated by reference. Advantageously, the secondary crosslinker frequently is added in the form of a solution in water, organic solvents or mixtures thereof, particularly in those cases where low amounts of secondary crosslinking agent are used. Suitable mixing apparatus for applying the secondary crosslinking agent are, e.g., Patterson-Kelley mixers, DRAIS turbulence mixers, Lödige mixers, Ruberg mixers, screw mixers, pan mixers, and fluid-bed mixers, as well as continuously operated vertical mixers wherein the powder is mixed at a rapid frequency using rotating knives (Schugi mixer). Once the surface crosslinker has been mixed with the crosslinked polymer, heating to temperatures of from 60 to 250° C., preferably from 135 to 200° C., and more preferably from 150 to 185° C. is effected in order to perform the surface crosslinking reaction. The time period of the heat treatment is limited by the risk of destroying the desired pattern of properties of the superabsorbent polymer product as a result of heat damage.

Depending on the type of use, various screening fractions are employed for processing the polymer products as superabsorbers, e.g. between 100 and 1000 µm and preferably between 150 and 850 µm for diapers. In general, this grain fraction is produced by milling and screening prior to and/or subsequent to secondary crosslinking.

According to the process of the invention, the cyclodextrins or derivatives thereof are employed as substance or dissolved in a solvent. A preferred solvent is water, but mixtures of water and organic solvents such as ethyl alcohol, acetone are also used.

The addition of the cyclodextrin component can be effected at various process stages in the production of the polymer products according to the invention. The amount of cyclodextrins or derivatives thereof is 0.01–50 wt.-%, preferably 0.1–30 wt.-%, and more preferably 0.5–10 wt.-%, relative to the amount of polymer product.

Thus, addition to the monomer solution is possible, where the cyclodextrin or its derivative is added directly to the aqueous monomer solution prior to the polymerization thereof. In case the polymer product of the invention is produced by suspension polymerization, it is also possible to pre-charge all or part of the cyclodextrin in the oil phase and meter the monomer solution thereto. Where only a part of the cyclodextrin is pre-charged, the remainder can be introduced via the monomer solution.

It is also possible to apply the cyclodextrin component onto a non-dried polymer gel, where the cyclodextrin or its derivative as substance or dissolved in water and/or an organic solvent is applied onto the crushed polymer gel, preferably by spraying and mixing.

However, it is also possible to dry and crush the polymer gel initially, and subsequently apply the cyclodextrin or its derivative as substance or dissolved in water and/or an organic solvent onto the powder. The resulting product immediately can be processed further or dried to remove solvents.

The cyclodextrin component may also be added onto the crushed and dried absorbent material during surface crosslinking of the polymer product. Suitable mixing apparatus for applying the crosslinking agent and the cyclodextrin component are e.g. Patterson-Kelley mixers, DRAIS turbulence mixers, Lödige mixers, Ruberg mixers, screw mixers, pan mixers, and fluid-bed mixers, as well as continuously operated vertical mixers wherein the powder is mixed at a rapid frequency using rotating knives (Schugi mixer).

Also, the cyclodextrin component can be applied onto the crushed, already surface-crosslinked polymer product. In this process variant, according to the invention, preferably ionically modified cyclodextrins as substance or dissolved in water and/or an organic solvent are sprayed onto the preferably powdered polymer, followed by evaporating the solvent.

According to the process of the invention, the cyclodextrin component may also be introduced at various stages of the production process, so as to optionally optimize its effect. In this way it is possible, for example, to polymerize a non-modified cyclodextrin together with the monomer solution and fix an ionically modified cyclodextrin on the surface of the polymer during surface crosslinking.

It is also possible to bind the cyclodextrin component to the polymer in an additional surface crosslinking.

Using the methods according to the invention, final products are obtained wherein the cyclodextrin or its derivative is incorporated in the synthetic polymer in such a way that the amount of cyclodextrin extractable with water is significantly less than the amount actually contained in the final product. In the products according to the invention, the extractable percentage of cyclodextrins is below 85% of the amount present in the product, preferably 60%, and more preferably 45%.

Owing to their excellent absorptive capacity, the polymer products of the invention are suitable as absorbents which, compared to powdered absorbents including no cyclodextrin or derivative thereof, exhibit improved absorption of malodorous compounds.

The polymers according to the invention find use e.g. in hygiene articles capable of absorbing body fluids such as urine, or in the packaging sector, e.g. meat and fish products, where they absorb large amounts of aqueous liquids and body fluids such as urine or blood, with swelling and formation of hydrogels. The polymer products of the invention are incorporated directly as powders in constructions for absorbing liquids, or previously fixed in foamed or non-foamed sheet materials. For example, such constructions for absorbing liquids are diapers for babies, incontinence articles or absorbent inserts in packaging units for foodstuffs.

Moreover, the absorbents of the invention were found to be excellently suited for incorporating active substances. The stability of sensitive active substances, e.g. with respect to oxidative degradation, is substantially improved as a result of incorporation in the absorbents of the invention.

Furthermore, the polymers according to the invention find use in plant breeding and in pest control in agriculture. In plant breeding, the polymers in the vicinity of plant roots provide for sufficient supply of liquid and previously incorporated nutrients and are capable of storing and releasing same over a prolonged period of time.

In pest control, the polymers can incorporate single active substances or a combination of multiple active substances which in use are released in a controlled fashion in terms of time and amount.

Production and properties of the polymer products according to the invention will be illustrated in the following Examples which also comprise the production of ionic cyclodextrins used according to the invention.

Test Methods used on Polymers According to the Invention 1) 180 ml of an aqueous solution of sodium chloride is poured over 1 g of polymer product, and this is stirred thoroughly for 1 hour (alternatively 16 hours) at room temperature. This is subsequently filtrated through a screen, and the concentration of cyclodextrin is determined according to the method below. This method is based on the reduction of light absorption (550 nm) of an alkaline solution of phenolphthalein in the presence of cyclodextrin which, as described by T. Takeuchi and T. Miwa, Chromatographia 1994, 38, 453, can be determined. The concentration obtained experimentally is divided by the concentration calculated theoretically. The theoretical concentration can be determined from the amount of cyclodextrin employed in the powder by dividing by 180. In this way, the extracted amount of cyclodextrin is obtained.

$$EA(CD) = \frac{\text{Concentration } (CD) \text{ found}}{\text{Theoretical concentration } (CD)}$$

EA(CD): extractable percentage of cyclodextrin.

2) Determination of the absorption of malodorous compounds 0.1 g of powdered polymer product is added with 2 ml of an aqueous solution (including 5 wt.-% ethanol) of malodorous compound, and this is sealed in a 5 ml test vessel. This is allowed to stand at 40° C. for 20 minutes, and the content of malodorous compound in the vapor space above the liquid is determined quantitatively against a blank using headspace GC.

EXAMPLES

Comparative Example 1 According to Patent Applications WO 94/22500 and WO 94/22501

9.850 g of a commercially available absorbent (Favor®, company Stockhausen GmbH) is mixed thoroughly with 0.15 g of solid β-cyclodextrin (beta-W7-cyclodextrin, technical grade, by Wacker company). Thereafter, the extractable amount of cyclodextrin is determined according to the specified test method.
EA=93%

Comparative Example 2 According to Patent Applications WO 94/22500 and WO 94/22501

40 g of polyethylene glycol (m.w. 3000) is melted at elevated temperature. 40 g of cyclodextrin is added thereto, and the mixture is homogenized. 9.40 g of a commercially available powdered absorbent (Favor®, company Stockhausen GmbH) is sprayed with 0.6 g of the cyclodextrin/polyethylene glycol solution, mixed thoroughly and cooled to room temperature. Thereafter, the extractable amount of cyclodextrin is determined according to the specified test method.
EA=89%

Example 1

A) An aqueous solution of acrylic acid (29.3 wt.-%) is mixed with 1.2 wt.-%/monomer of a polyglycol acrylate crosslinker mixture and partially neutralized to 60 mole-% using a 50% sodium hydroxide-solution with stirring and cooling. The solution is cooled to 7–8° C. and purged with nitrogen for about 20 minutes. Following addition of aqueous solutions of sodium persulfate, hydrogen peroxide and a water-soluble azo initiator, the polymerization is initiated with ascorbic acid, whereupon a significant rise in temperature to more than 90° C. occurs. A gel-like product is obtained.

B) 50 g of the dried and milled polymer from A) screen to 150–800 μm is wetted with a solution of 0.5 g of ethylene carbonate, 2 g of water and 4 g of acetone in a plastic vessel with vigorous stirring and mixed thoroughly using a commercially available household hand mixer (Krups company). Subsequently, the wetted polymer is heated in an oven at a temperature of 180° C. for 30 minutes, thereby undergoing surface crosslinking.

C) The procedure is as described in A). In addition, however, 5 g of cyclodextrin is added to the monomer solution. A gel-like product is obtained, the further processing of which is effected as described in B).

D) The gel free of cyclodextrin, which has been obtained in A), is immersed in a 80° C. hot solution in a beaker, consisting of 10 g of cyclodextrin and 23.3 g of water, until the solution has completely permeated into the polymer gel. Subsequently, the gel is willowed and dried at 150° C.

EA=27%, determined according to the specified test method.

E) 50 g of the dried and milled polymer from D) screened to 150–800 mm is wetted with a solution of 0.5 g of ethylene carbonate, 2 g of water and 4 g of acetone in a plastic vessel with vigorous stirring and mixed thoroughly using a commercially available household hand mixer (Krups company). Subsequently, the wetted polymer is heated in an oven at a temperature of 180° C. for 30 minutes.

The extractable percentage, EA=8%, determined according to the specified test method, is clearly lower as a result of surface crosslinking.

Example 2

50 g of the willowed, dried and milled polymer from Example 1A) screened to 150–800 μm is wetted with a solution of 0.5 g of ethylene carbonate, 1.5 g of non-modified cyclodextrin, and 8.5 g of water in a plastic vessel with vigorous stirring and mixed thoroughly using a commercially available household hand mixer (Krups company). For surface crosslinking, the wetted polymer subsequently is heated in an oven at a temperature of 175° C. for 25 minutes.
EA=80%, determined according to the specified test method.

Example 3

F) In a 500 ml three-necked round bottom flask, 113.4 g of β-cyclodextrin is suspended in 200 g of deionized water and 8 g of an aqueous sodium hydroxide solution (50%). This suspension is heated to boiling until all of the above is dissolved. With vigorous stirring, 34.4 g of an aqueous solution of DIMAPA-quat. (60%) is added dropwise over 30 min, and this is stirred under reflux for another 5 hours. The solution is cooled to 5° C., and a pH of 7 is adjusted using hydrochloric acid. The precipitate is filtrated and washed with water. Following drying of the filter residue, the DS value is determined to be 0.005 using elemental analysis. 50 g of the willowed, dried and milled polymer from Example 1 B) screened to 150–800 μm is wetted with a solution of 0.5 g of ethylene carbonate, 1.5 g of cyclodextrin derivative according to F), and 7.3 g of water in a plastic vessel with vigorous stirring and mixed thoroughly using a commercially available household hand mixer (Krups company). For surface crosslinking, the wetted polymer subsequently is heated in an oven at a temperature of 175° C. for 25 minutes.

EA=40%, determined according to the specified test method.

Determination of the Gas Concentration of Malodorous Compounds

Superabsorbers made of polyacrylic acid with a degree of neutralization of 60% and 70%, respectively, and subjected to secondary surface crosslinking were modified in a second secondary surface crosslinking according to the procedure of Example 3, using various cyclodextrins. The amount of cyclodextrin can be inferred from the following Table. In the measurement of malodorous substances, a polymer with no cyclodextrin was tested as a blank according to the specified test procedure, and the gas concentration of malodorous substance found was set 100%. Samples containing cyclodextrin were subsequently tested and the gas concentration of malodorous substance determined.

Odorous Substance: Ethylfuran.

| Wt. - % CD | Cyclodextrin derivative | Reduction of ethylfuran concentration in the gaseous space |
|---|---|---|
| 10## | β-Cyclodextrin | 72% |
| 3## | β-Cyclodextrin | 63% |
| 3## | α-Cyclodextrin | 68% |

Absorber having 60% neutralization of the acid groups

As can clearly be seen, the gas concentration of volatile substances dissolved in water is reduced upon absorption by the cyclodextrin-containing polymers of the invention.

In analogy to ethylfuran, an odorous substance containing sulfur was tested.

In addition, the effect of pure cyclodextrin (with no polymer) was monitored. As can be seen, cyclodextrin in the polymer of the invention from a content as low as 3% on achieves a marked reduction in the gas concentration of the sulfur-containing compound.

Doping with Furfurylmercaptane:

| Wt. - % CD | Cyclodextrin or CD derivative | Reduction of furfurylmercaptane concentration in the gaseous space |
|---|---|---|
| 10# | β-Cyclodextrin | 42% |
| 3# | β-Cyclodextrin | 51% |
| 3# | α-Cyclodextrin | 65% |
| 10## | β-Cyclodextrin | 46% |
| 3## | β-Cyclodextrin | 18% |
| 3## | α-Cyclodextrin | 28% |
| 1.5# | Monochlorotriazinyl-β-cyclodextrin | 42% |
| 3# | Monochlorotriazinyl-β-cyclodextrin | 49% |
| 100 | β-Cyclodextrin | 57% |
| 100 | α-Cyclodextrin | 64% |

Absorber having 70% neutralization of the acid groups
Absorber having 60% neutralization of the acid groups The polymers of the invention develop excellent effectiveness when the cyclodextrin is entrapped in the polymers:

| Polymer of Example | CD ratio [wt. - %] | CD derivative | Reduction of furfurylmercaptane concentration in the gaseous space (%) |
|---|---|---|---|
| 1 E | 1.5 | non-modif. | 72 |
| 1 E | 3 | non-modif. | 55 |
| 3 | 3 | of Ex. 3F | 49 |

What is claimed is:

1. A sheet material comprising absorptive polymer particles comprising one or more polymers comprising polymerized units of one or more monoethylenically unsaturated monomers having at least one acid group,
   wherein the surface of the absorptive polymer particles is secondary surface crosslinked, and
   wherein the polymer is at least partially neutralized and has one or more cyclodextrins, cyclodextrin derivatives, or both cyclodextrins and cyclodextrin derivatives, bonded covalently thereto, bonded ionically thereto, incorporated therein or a combination thereof.

2. The sheet material according to claim 1, wherein the polymer comprises from 0.01 to 50 wt. % of at least one of the cyclodextrins, cyclodextrin derivatives or mixture thereof, based on the total weight of the polymer.

3. The sheet material according to claim 1, wherein at most 85 wt. % of the cyclodextrins or cyclodextrin derivatives are extractable from the polymer with water.

4. The sheet material according to claim 2, wherein at most 85 wt. % of the cyclodextrins or cyclodextrin derivatives are extractable from the polymer with water.

5. The sheet material according to claim 3, wherein at most 60 wt. % of the cyclodextrins or cyclodextrin derivatives are extractable from the polymer with water.

6. The sheet material according to claim 1, wherein the polymer further comprises up to 40 wt. % of one or more further monoethylenically unsaturated monomers different from the monoethylenically unsaturated monomers having an acid group relative to the polymer.

7. The sheet material according to claim 1, wherein the polymer comprises from 0.05 to 3 wt. % of one or more polymerized units of a cross-linking monomer relative to the polymer.

8. The sheet material according to claim 1, comprising up to 30 wt. % of at least one of a copolymerized or graft polymerized water soluble, natural or synthetic polymer relative to the polymer.

9. The sheet material according to claim 1, wherein the polymer particles are surface cross-linked with from 0.1 to 10 wt. % of one or more cross-linking components relative to the polymer.

10. The sheet material according to claim 1, wherein the polymer comprises at least one of an α-cyclodextrin, a β-cyclodextrin, a γ-cyclodextrin, or a derivative thereof.

11. The sheet material according to claim 1, wherein the polymer has a sieve fraction with a particle size in the range of from 100 to 1000 $\mu$m.

12. The sheet material according to claim 1, wherein the polymer particles are present on the surface of the sheet.

13. A diaper comprising the sheet material according to claim 1.

14. An incontinence article comprising the sheet material according to claim 1.

15. A method comprising
contacting a liquid with the sheet material according to claim 1 to absorb the liquid and reduce the odor of the liquid.

16. The method of claim 15, wherein the liquid is a human bodily fluid.

17. The method as claimed in claim 15, wherein the sheet material is a packaging unit.

18. The method as claimed in claim 15, wherein the sheet material is a diaper.

19. The sheet material according to claim 1, wherein the absorptive polymer particles are obtained by first polymerizing to form a polymer then subsequently crosslinking the surface of the polymer.

20. Polymers based on crosslinked monomers bearing partially neutralized acid groups, the surface of which has been surface crosslinked folling polymerization, obtained by a process wherein an aqueous solution containing partially neutralized acrylic acid is converted to a gel in the presence of crosslinkers and optional polymer additives;

the gel is subsequently dried, milled and screened to the desired particle size;

the polymer is surface cross-linked before or after the gel has been dried wherein cyclodextrines or derivatives thereof as a substance or dissolved in a solvent are added directly to the aqueous monomer solution prior to the polymerization thereof;

are applied to a non-dried polymer gel;

are added onto the crushed and dried absorbent material during surface corsslinking of the polymer product;

are applied onto the crushed, already surface crosslinked polymer product.

21. A sheet material comprising the polymer of claim 20.

22. The sheet according to claim 21, wherein the sheet material is a diaper.

23. A polymer comprising polymerized units of one or more monomers having at least partially neutralized acid groups, wherein the polymer is a crosslinked polymer obtained by polymerizing an aqueous solution comprising at least partially neutralized acrylic acid and one or more crosslinkers, to form a gel, drying the gel, milling and screening the dried gel, adding one or more cyclodextrins or derivatives thereof as a solid or as a solution in a solvent, and surface crosslinking the gel.

24. The polymer of claim 23, wherein the surface crosslinking is carried out before the drying.

25. The polymer of claim 23, wherein the surface crosslinking is carried out after the drying.

26. The polymer of claim 23, wherein the cyclodextrins or derivatives thereof are added to the aqueous solution prior to the polymerizing.

27. The polymer of claim 23, wherein the cyclodextrins or derivatives thereof are added to the polymer gel before the drying.

28. The polymer of claim 23, wherein the cyclodextrins or derivatives thereof are added to the dried, milled and screened gel during crosslinking.

29. The polymer of claim 41, wherein the cyclodextrins or derivatives thereof are added to the dried, milled and screened gel after crosslinking.

30. A sheet material comprising the polymer of claim 23.

31. The sheet according to claim 23, wherein the sheet material is a diaper.

* * * * *